United States Patent [19]
Woo

[11] 4,404,381
[45] Sep. 13, 1983

[54] NOVEL 3,5-DIKETO-PIPERAZINYL COMPOUNDS CONTAINING EPOXIDE SUBSTITUTED IMIDES

[75] Inventor: Edmund P. Woo, Midland, Mich.

[73] Assignee: The Dow Chemical Company, Midland, Mich.

[21] Appl. No.: 275,471

[22] Filed: Jun. 19, 1981

[51] Int. Cl.³ .............................................. C07D 241/02
[52] U.S. Cl. ................................... 544/357; 156/330
[58] Field of Search ........................................ 544/357

[56] References Cited

U.S. PATENT DOCUMENTS

| | | | |
|---|---|---|---|
| 2,772,296 | 11/1956 | Mueller et al. | 260/348 |
| 3,078,271 | 2/1963 | DeGroote et al. | 544/357 |
| 3,196,153 | 7/1965 | Dazzi | 544/357 |
| 3,377,316 | 4/1968 | Reinking et al. | 544/357 |
| 3,792,018 | 2/1974 | Logan | 544/357 |
| 3,914,288 | 10/1975 | Garnish et al. | 544/357 |
| 3,936,456 | 2/1976 | Ramey et al. | 544/357 |

FOREIGN PATENT DOCUMENTS 1234935  6/1971  United Kingdom ................ 544/357

OTHER PUBLICATIONS

Morrison et al., "Organic Chemistry," 3rd Ed., (1973), pp. 562–563, Allyn & Bacon, Inc. Boston, Mass.

*Primary Examiner*—Robert Gerstl
*Assistant Examiner*—S. A. Gibson
*Attorney, Agent, or Firm*—Michael L. Glenn; Norman L. Sims

[57] ABSTRACT

Certain novel diepoxides derived from an alkylenediaminetetraacetic acid are described. These diepoxides can be reacted with standard curing agents to prepare coatings or films possessing good weatherability.

4 Claims, No Drawings

NOVEL 3,5-DIKETO-PIPERAZINYL COMPOUNDS CONTAINING EPOXIDE SUBSTITUTED IMIDES

BACKGROUND OF THE INVENTION

This invention relates to a novel diepoxide compound and to a process for making this compound. In particular, this invention relates to a diepoxide derived from an alkylenediaminetetraacetic acid.

Diepoxide compounds, such as the diglycidyl ether of bisphenol A, are used in the prior art to prepare coatings, films and molded articles. However, resins prepared from aromatic epoxide compounds are deleteriously affected by sunlight. On the other hand, the cycloaliphatic epoxide compounds generally employed in resins exposed to actinic rays are slow to cure. The instant diepoxides avoid these deficiencies of the prior art epoxide compounds.

U.S. Pat. No. 2,772,296 teaches the preparation of an epoxide compound by the reaction of a carboxylic acid with an epihalohydrin. A quaternary phosphonium or ammonium salt is used as a catalyst.

SUMMARY OF THE INVENTION

Novel diepoxide compounds have now been prepared which correspond to the formula

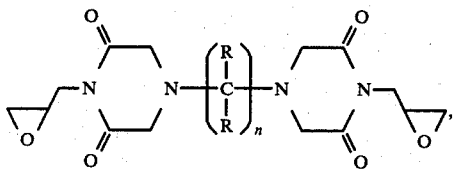

wherein each R is independently hydrogen or a $C_1$ to $C_{12}$ alkyl group and n is an integer from 2 to 20. These diepoxides are prepared in a process comprising the steps of:

(a) reacting in the liquid phase the diimide corresponding to the formula

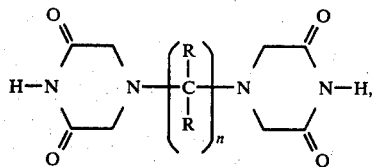

with at least about 2 equivalents of a base so as to produce a divalent salt corresponding to the formula

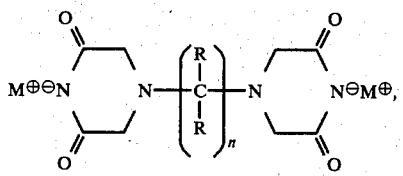

wherein $M^\oplus$ is an alkali metal or alkaline earth metal cation;

(b) recovering the divalent salt produced in step (a); and (c) reacting in the liquid phase the divalent salt recovered in step (b) with from about 3 to about 20 equivalents of an epihalohydrin in the presence of a catalytic amount of a quaternary ammonium or phosphonium salt or a crown ether, so as to produce the aforementioned diepoxide compound.

DETAILED DESCRIPTION OF THE INVENTION

Diimide:

The reaction of an alkylenediaminetetraacetic acid with formamide to produce a diimide is taught in British Pat. No. 1,234,935, the relevant portions of which are incorporated by reference. Alkylenediaminetetraacetic acids corresponding to the formula

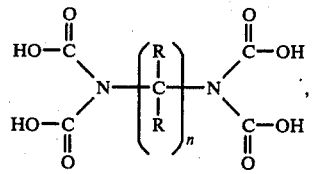

wherein R and n can take the aforementioned identities, form a well-known class of compounds which can be readily prepared by standard methods known in the art. Especially, preferred are those compounds in which at least one of the R groups on each of the carbon atoms joining the amine groups is hydrogen. Preferably, n in the foregoing formulas is an interger from 2 to about 6. Most preferred is ethylenediaminetetraacetic acid.

The reaction of the alkylenediaminetetraacetic acid with formamide is preferably performed neat, but can also be performed in a liquid diluent which is inert to the instant reactants. Suitable diluents include N-methylpyrolidinone, N,N-dimethylformamide, dimethyl sulfoxide and bisethers of polyalkylene oxides, such as, diethylene glycol methyl ether and dipropylene glycol methyl ether.

The reactants are conveniently employed in their stoichiometric ratio, i.e., two moles of formamide for each mole of alkylenediaminetetraacetic acid. However, in one preferred embodiment an excess of formamide is employed to serve as a solvent.

The reaction temperature is advantageously high enough to distill water and other by-products produced in the formation of the diimide. Generally, temperatures of at least about 100° C. afford convenient rates of reaction. The progress of the reaction can be monitored by the quantity of the by-products recovered overhead. The pressure during the reaction is not critical, but sub-atmospheric pressures are preferred.

The diimide product can be conveniently recovered from the reaction mixture by distillation to remove unreacted starting materials and any more volatile products overhead. The crude diimide in the undistilled residue can be purified by recrystallization in a manner known in the art. Methanol is the preferred solvent for recrystallization.

Step (a)

The diimide is reacted in a liquid medium with a base capable of abstracting a proton from each of the nitrogen groups of the diimide. Preferred bases include alkali metal or alkaline earth metal hydroxide, oxide or alkoxide salts. Other materials having sufficient basic character to abstract a proton from the diimide are also operable. The most preferred bases are sodium hydroxide or potassium hydroxide.

Conveniently, a polar compound which dissolves the diimide is employed as a liquid diluent. The diluent should be a liquid at the instant reaction conditions and should be inert to the diimide and base employed. Preferred liquid diluents include water, a $C_1$ to $C_4$ alkanol, formamide, $C_2$ to $C_4$ dialkylsulfoxide and an amide of a $C_2$ to $C_4$ alkanoic acid. Water is particularly preferred as a solvent.

The reaction temperature for the conversion of the diimide to the corresponding divalent salt is generally not critical so long as the medium is liquid and the temperature is not so high as to cause significant hydrolysis or decomposition of the diimide. However, a temperature of no greater than about 15° C. is preferred. Temperatures of from about 0° C. to about 15° C. are most preferred.

The diimide and base are preferably present in the stoichiometric ratio. With some of the weaker bases and excess of the base may be advantageous. Generally, an excess of the diimide is not desirable, because monovalent salts will be formed.

Step (b)

The divalent salt of the diimide is conveniently recovered by adding a nonpolar compound miscible with the polar solvent, so as to precipitate the salt. Tetrahydrofuran is preferred as a nonpolar solvent. Other known methods can also be employed to isolate the divalent salt. For example, where stoichiometric quantities of the base and diimide are employed, the salt may be recovered by distillation or evaporation of the polar solvent.

Step (c)

The divalent salt of the diimide reacts at from about 30° C. to about 120° C. in a liquid medium with an excess of an epihalohydrin in the presence of a catalytic amount of a phase-transfer catalyst to produce the corresponding diepoxide. The epihalohydrin can be epichlorohydrin or epibromohydrin, with epichlorohydrin being preferred.

The aforementioned reaction is advantageously conducted in the presence of a greater than stoichiometric quantity of the epihalohydrin. Preferably, a 100 mole percent to a 2000 mole percent excess of the epihalohydrin is present in the reaction mixture. In this preferred embodiment, the epihalohydrin serves as a diluent as well as a reactant. Other diluents which unlike the epihalohydrin are inert in the reaction may also be employed, but are neither necessary nor advantageous.

The reaction temperature can vary over a wide range, but a temperature of at least about 30° C., preferably at least 50° C. is preferred to provide an economical rate of reaction. The upper temperature limit is set by the boiling point of the epihalohydrin reactant. Superatmospheric pressures can be utilized to enable the use of temperatures higher than 120° C., but this practice is not believed to be advantageous because atmospheric or sub-atmospheric pressures are more convenient. An atmosphere inert in the reaction of the epihalohydrin with the diimide salt is preferred. A nitrogen atmosphere above the liquid reaction mixture is preferred.

The catalysts employed to promote the reaction of the epihalohydrin with the diimide salt are generally categorized as phase-transfer catalysts. These catalysts include quaternary ammonium and phosphonium salts as well as crown ethers. Exemplary of the quaternary ammonium salts are benzyltrimethylammonium chloride or bromide, benzyltriethylammonium chloride or bromide, dibutyldimethylammonium chloride, tetramethylammonium bromide, tetrabutylammonium bromide or chloride, and tetraethylammonium chloride. Illustrative examples of the quaternary phosphonium salts are tetraphenylphosphonium bromide or chloride, ethyltriphenylphosphonium acetate acetic acid, tri-n-butyl(1,2-dicarboxyethyl)phosphonium hydroxide inner salt, and ethyltriphenylphosphonium bicarbonate. The crown ethers are macrocyclic polyethers which are illustrated by dibenzo-18-crown-6, dicyclohexyl-18-crown-6 and 18-crown-6. Additional phase-transfer catalysts are described in W. P. Weber et al., *Phase-Transfer Catalysis in Organic Synthesis,* Springer-Verlag (1977) and U.S. Pat. No. 2,772,296, the relevant portions of which are incorporated herein by reference. The phase-transfer catalyst should be employed in a quantity effective to catalyze the epoxidation of the diimide salt. Generally, a concentration of from about 0.5 to about 5 mole percent of this catalyst based on the moles of divalent salt of the diimide present is used to advantage.

The time required for maximum conversion to the diepoxide will vary dependent on the identity of the diimide salt and the catalyst as well as the reaction temperature and other operating parameters. Typically, from about 2 to about 10 hours will elapse before equilibrium is reached.

The diepoxide compound can be isolated by any one of numerous methods known in the prior art. Conveniently, the reaction medium is cooled to room temperature and extracted with an organic solvent in which the diepoxide is soluble and stable, such as dichloromethane. The organic solvent is washed several times with water and then residual water is removed from the solvent with a drying agent. The dried organic solvent can be distilled to yield a crude diepoxide residue. The diepoxide can be purified by recrystallization or by other techniques known to the prior art.

Utility

The diepoxide derived from an alkylenediaminetetraacetic acid can be reacted in the conventional manner with a polyhydric phenol in the presence of a quaternary ammonium or phosphonium catalyst to prepare advanced epoxy resins useful in making coatings, films and molded or encapsulated articles. Preferred polyhydric phenol reactants are those corresponding to the formula

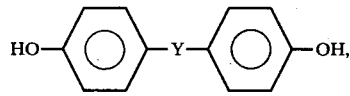

wherein Y is a $C_1$ to $C_3$ alkylene, $C_2$ to $C_3$ alkylidene or —S—. The method for reacting a diepoxide with a polyhydric phenol is more fully described by Lee and Nevill, *Handbook of Epoxy Resins,* McGraw-Hill Book Co. (1967).

The instant diepoxide and epoxy resins prepared therefrom rapidly cure in the presence of standard curing agents. Illustrative curing agents include, 4,4'-methylenedianiline, hexamethylenetetramine and phthalic anhydride. Generally, no accelerator is required to promote curing of the resin at elevated temperatures, i.e., temperatures greater than about 100° C. In its molten state the instant diepoxides typically have a low viscosity and are therefore well-suited for use in powder coatings.

The following example is presented to illustrate the instant invention.

EXAMPLE 1

To a reaction vessel equipped with a stirrer and thermometer is charged 8 grams (0.2 mole) of NaOH and 250 milliliters (ml) of H₂O. To the vessel is added 25.4 grams (0.1 mole) of 3,5,3′,5′-tetraoxo-1,2-dipiperazinoethane. The reaction mixture is stirred and maintained at a temperature of about 15° C. After all the solid has ostensibly dissolved, 1 liter of tetrahydrofuran is introduced to the reaction mixture with vigorous agitation. A resulting white crystalline material precipitates from solution and is isolated by filtration. The crystalline material is dried under reduced pressure at 80° C. to a weight of 28.9 grams. This material is determined by conventional methods of analysis to be the disodium salt of the diimide starting material. The isolated product represents a 97 percent yield.

To a second reaction vessel is charged 15 grams (0.05 mole) of the disodium salt of the diimide, 70 grams (0.757 mole) of epichlorohydrin and 0.15 gram of benzyltriethylammonium chloride. This reaction mixture is vigorously stirred and refluxed under a nitrogen atmosphere for 2 hours. The reaction mixture is cooled to room temperature and 200 ml of dichloromethane is introduced. The dichloromethane solution is washed 5 times with 100-ml portions of H₂O. After drying with anhydrous MgSO₄, the dichloromethane solution is distilled at reduced pressure to leave a waxy residue. The waxy solid is washed with methanol to give a crystalline solid. This solid is identified as the diepoxide of the diimide and is recovered in 30 percent yield.

What is claimed is:

1. A compound corresponding to the formula

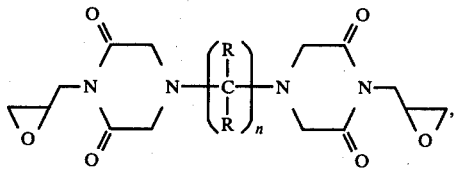

wherein each R is independently hydrogen or a C₁ to C₁₂ alkyl group and n is an integer from 2 to 20.

2. The compound as described in claim 1 wherein at least one R on each of the carbon atoms joining the amine groups is hydrogen.

3. The compound as described in claim 1 wherein R is hydrogen at each occurrence.

4. The compound as described in claim 3 wherein n is the integer 2.